United States Patent [19]

Wehrli

[11] 4,079,076
[45] Mar. 14, 1978

[54] NOVEL CYANO COMPOUNDS

[75] Inventor: Pius Anton Wehrli, North Caldwell, N.J.

[73] Assignee: Hoffmann-La Roche, Inc., Nutley, N.J.

[21] Appl. No.: 667,796

[22] Filed: Mar. 17, 1976

Related U.S. Application Data

[63] Continuation-in-part of Ser. No. 566,589, Apr. 9, 1975, abandoned.

[51] Int. Cl.$^2$ .......................................... C07C 120/00
[52] U.S. Cl. .................................. 260/465.4; 260/464; 260/465 R; 260/465 D; 260/465 F; 260/465 G; 260/465.1; 260/465.6; 260/465.7; 260/465.9; 260/617 R; 260/632 N; 424/311; 424/343; 560/262; 560/241
[58] Field of Search ............... 260/464, 465 D, 465 F, 260/465.1, 465.9, 465 R, 465.4

[56] References Cited

U.S. PATENT DOCUMENTS

| | | | |
|---|---|---|---|
| 2,453,824 | 11/1948 | Wood | 260/465.4 X |
| 2,483,853 | 10/1949 | Smith et al. | 260/465.4 |
| 3,347,930 | 10/1967 | Freyschlag et al. | 260/602 |
| 3,367,961 | 2/1968 | Brewbaker | 260/465.4 R |
| 3,442,935 | 5/1969 | Pine et al. | 260/465.4 X |
| 3,637,816 | 1/1972 | Honjoh et al. | 260/488 H |
| 3,962,053 | 6/1976 | Kornblum | 260/465.4 X |

FOREIGN PATENT DOCUMENTS

| | | |
|---|---|---|
| 1,294,372 | 5/1969 | Germany. |
| 1,169,438 | 5/1964 | Germany. |
| 1,358,121 | 6/1974 | United Kingdom. |

OTHER PUBLICATIONS

C.A., Salimov et al.; 84, (1976), 58705.
Kabaivanov et al., "Godishnik na Khimiko Technologicheskiya Institut," vol. 2, p. 211 relied on.
Rappoport, The Chemistry of the Cyano Group, 1970, Interscience Publishers, pp. 806–807.

*Primary Examiner*—Joseph Paul Brust
*Attorney, Agent, or Firm*—Samuel L. Welt; Bernard S. Leon; Richard A. Gaither

[57] ABSTRACT

A novel conjugated diene bisfunctionalization process wherein a nitro group and a hydroxyl group in the form of an ester are introduced into the conjugated diene molecule by treatment of conjugated dienes with nitric acid in the presence of an acid anhydride. The novel compounds produced by this process and transformation products thereof, are useful as bactericides and fungicides and valuable organic synthesis intermediates, A novel procedure for the production of nitriles and γ-acetoxytiglic aldehyde is disclosed.

7 Claims, No Drawings

NOVEL CYANO COMPOUNDS

CROSS REFERENCE TO RELATED APPLICATIONS

This application is a continuatio-in-part application of U.S. patent application Ser. No. 566,589, filed Apr. 9, 1975, entitled NOVEL ISOPRENE DERIVATIVES, now abandoned.

BACKGROUND OF THE INVENTION

Conjugated dienes, particularly isoprene, are basic building blocks of natural and synthetic rubber. As a matter of fact, the $C_5$ structure of isoprene is the basic unit of many natural products. Natural products whose structures are composed of isoprene units are referred to as isoprenoids. While isoprene itself has not been encountered in nature, the biogenetic path of synthesis of the terpenes involves the incorporation of the $C_5$ repeating unit into a large variety of open and ring structures. The isoprene molecule is, therefore, of considerable importance in the synthesis of natural products. .

Attempts to synthesize natural products from isoprene normally involve the functionalization of isoprene. Successful functionalizations of isoprene have involved the addition of anhydrous HCl to isoprene yielding a mixture of prenyl chloride and isoprenyl chloride, the direct halogenation of isoprene yielding mixtures of dihalomethylbutenes, and reaction with tosyl chloride to give positional and cis/trans isomer mixtures of $C_5$ chlorosulfones. The utility of the halogenated isoprenes, however, is quite limited due to the difficulty of replacing the halogen substituents selectively with other functional groups. In view of the considerable interest in the synthesis of natural products and other materials employing the isoprenoid unit, there is a continuing effort in the area of isoprene functionalization.

It has been found that isoprene and other conjugated dienes can be regiospecifically difunctionalized according to the process disclosed and claimed herein. The novel compounds, because of the presence of the nitro group are readily amenable to the transformation of the nitro group to other functional groups, e.g., amino, carbonyl, cyano, oximes, etc. The presence of the alkoxy carbonyl (ester) moiety also provides another reactive site. One advantage is that the resultant products of the instant process are substantially in the transconfiguration, with regard to the disposition of the nitro and ester groups, as opposed to cis and trans mixtures, which are generally obtained when isoprene is bishalo substituted. Another important advantage is that the nitro group attaches itself practically exclusively at the one position of the conjugated diene carbon skelton thereby obviating the need to separate any positional isomeric species.

The isoprenoid structure also forms the basis of one of the starting materials in vitamin A synthesis, i.e., γ-acetoxytiglic aldehyde or derivatives thereof. There is a continuing effort to find new and economical ways to prepare this important starting material. (See, for example, Freyschlog et al., U.S. Pat. Nos. 3,347,930; 3,760,004; Himmele et al.; U.S. Pat. Nos. 3,661,980; 3,732,287; and 3,781,337). The instant invention provides a simple and economical way to obtain γ-acetoxytiglic aldehyde.

A surprising feature is that the regiospecific difunctionalization proceeds with negligible polymerization of the conjugated diene starting material. This is unexpected in view of the ready polymerizability of conjugated dienes in acidic solution and in the presence of radical initiators, such as nitrous oxides, which cannot be excluded whenever nitric acid is employed.

Although the foregoing discussion has been directed to isoprene, it is equally applicable to conjugated dienes in general.

SUMMARY OF THE INVENTION

The process of the instant invention is carried out by treating a conjugated diene of the formula:

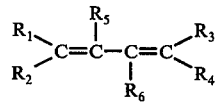

with nitric acid in the presence of an acid anhydride, preferably acetic anhydride, to form products of the formulas:

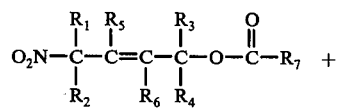

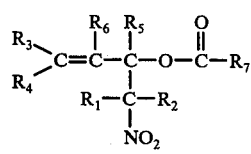

wherein $R_1$, $R_2$, $R_3$, $R_4$, $R_5$, $R_6$ are hydrogen or lower alkyl, and $R_7$ is lower alkyl. In compound II either of the pair or $R_1$ and $R_3$ or $R_2$ and $R_4$ may be taken together to form a ring, when one of said pair is taken together to form a ring each member of the remaining pair is hydrogen or lower alkyl.

Compound III, in the presence of catalytic amounts of sulfuric acid alone or in combination with metal salts thereof, e.g., copper sulfate, can be rearranged to form compound II.

Compounds II and III may be subsequently transformed by hydrolysis to the respective alcohols by conventional procedures. The alcohols have the following formulas:

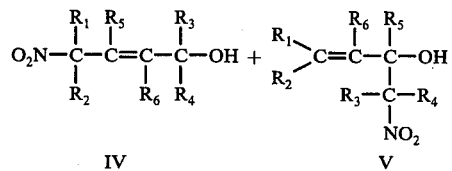

wherein $R_1$, $R_2$, $R_3$, $R_4$, $R_5$ and $R_6$ are as above. In compound IV either of the pair of $R_1$ and $R_3$ and $R_2$ and $R_4$ may be taken together to form a ring as previously described.

Compounds II–V have been found to possess antimicrobial, bactericidal, and fungicidal properties. These compounds are also useful as organic syntheses intermediates in general as well as polyene syntheses in particular.

The isomeric species of each of the above compounds are separable by conventional techniques such as distillation and chromatography.

DESCRIPTION OF THE INVENTION

As used throughout the specification, the term "acid anhydride" refers to compounds having the formula:

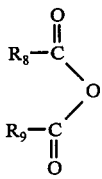

wherein $R_8$ and $R_9$, which may be the same or different, are alkyl.

The term "alkyl" refers to straight or branched chain hydrocarbon groups having from 1-20 carbon atoms, e.g., methyl, ethyl, propyl, butyl, octadecyl and the like. Especially preferred are lower alkyl groups wherein the above-mentioned chains contain from 1-6 carbon atoms. The term "lower alkanol" refers to straight or branched chain alcohols having from 1-6 carbon atoms. The term "alkylene" refers to straight or branched chain hydrocarbon groups have from 1-20 carbon atoms, e.g., methylene, propylene, butylene and the like. Especially preferred are lower alkylene groups wherein the above-mentioned chains contains from 1-6 carbon atoms. The term "alkoxy" refers to straight or branched chain alkoxy groups containing from 1-20 carbon atoms. Especially preferred are "lower alkoxy" groups containing from 1-6 carbon atoms. The term "acyloxy" refers to acyloxy groups having from 1-20 carbon atoms. Especially preferred are lower acyloxy groups having from 1-6 carbon atoms such as acetoxy, propionyloxy and the like. The term "alkoxycarbonyl" refers to alkoxycarbonyl groups wherein the alkoxy moiety contains from 1-20 carbon atoms, preferably 1-6 carbon atoms. Typical alkoxycarbonyl groups are methoxycarbonyl, ethoxycarbonyl and the like. The term "phenyl" refers to nuclear substituted or unsubstituted phenyl groups. Typical phenyl substituents may be halogen, lower alkoxy, nitro, nitromethyl and cyano. The terms halogen, unless otherwise stated, refers to bromine, chlorine, fluorine and iodine.

The difunctionalization is deemed to be regiospecific because the nitro group always adds at the 1-position of the isoprenoid moiety of compound I.

The regiospecifically difunctionalized conjugated dienes are formed by reacting said dienes with nitric acid in the presence of an acid anhydride, preferably acetic anhydride, at a temperature not exceeding 30° C., generally from about 15° C. to 30° C. The reation must be maintained at or below 30° C. to avoid violet decomposition of the nitro compounds. The reaction is generally conducted by adding the nitric acid to the acid anhydride with adequate cooling and subsequent addition of the conjugated diene. The conjugated diene is added slowly over a period of time such that the reaction temperature does not exceed 30° C. The clear yellow reaction mixture, after cooling, is poured into cold water, causing the nitro compound to separate out as a yellow oil heavier than water. The organic layer and water layer are subjected to conventional extraction, washing and drying procedures. The excess unreacted acid anhydride is removed by vacuum distillation. These nitro esters may then be transformed to their alcohols by hydrolysis with mineral acids, if desired.

The acid anhydride is generally employed in a molar excess of from about 5 to about 35 moles per mole of conjugated diene Although a lesser or greater excess may be employed, no particular advantages are realized thereby.

The amounts of nitric acid employed will generally vary from about 1 mole to 5 moles per mole of conjugated diene, preferably from about 1:1 to about 2:1.

The mixture of nitro esters, compounds II and III, may then be separated by conventional means, e.g., vapor phase chromatography, column chromatography (silica gel as adsorbent), distillation. Upon separation, the ratio of compound II to compound III is about 7:3.

If desired, the crude mixture of nitro esters may be subjected to rearrangement conditions, as indicated hereinbefore, whereby the resultant product is essentially all compound II having a trans to cis ratio of about 85:15. The cis and trans isomers are readily separable by the chromatographic procedures described hereinbefore.

The nitro esters of compounds II and III are useful as bactericides and fungicides.

Alternatively, the crude nitro esters may be hydrolyzed and the respective alcohols, compounds IV and V, separated by the conventional means described above. As stated hereinbefore, compounds IV and V have been found to possess bactericidal and fungicidal properties. In addition, compounds IV and V may also be used as intermediates in the production of alcohol derivatives such as ethers, esters, urethanes, etc.

Another embodiment of this invention is the preparation of amino, cyano and oxime analogues of compounds II-V and their corresponding alcohol derivatives. These particular analogues and their derivatives are useful as intermediates in the preparation of polyenes by known procedures. It is to be understood that both the cis and trans isomers of these analogues, as well as the alcohol derivatives of same, are embodiments of the instance invention.

The amino analogues of compound II, compound of the formula:

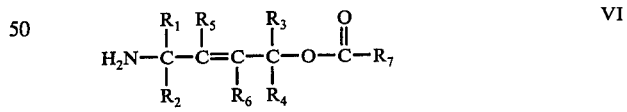

wherein $R_1$, $R_2$, $R_3$, $R_4$, $R_5$, $R_6$ and $R_7$ are as previously defined.
are prepared by reducing a compound of formula II in the presence of zinc powder. The reaction is carried out in solvents such as water, methanol, ethanol, and mixtures thereof in the presence of a mineral acid, e.g., HCl. Compound VI may either be prepared directly from compound II after separation from compound III or from a crude mixture of compounds II and III, followed by chromatographic purification, as described hereinbefore.

The oxime analogues of the primary nitro compound II, compounds of the formula:

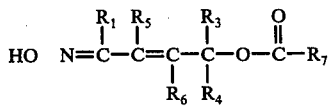

wherein $R_1 = H$, $R_3$, $R_4$, $R_5$, $R_6$ and $R_7$ are as defined above and the wavy line indicates that the oxime may be in either the syn or anti form, may generally be prepared by treating a compound of formula II, or a crude mixture of compounds II and III, with from about 1 to about 5 moles of metallic iron or magnesium in the presence of a lower alkyl mono-carboxylic acid, preferably acetic acid. Although the reaction temperature is not critical, the reaction temperature generally ranges from about room temperature to about 120° C., preferably 80°-90° C. The presssure is generally atmospheric pressure.

It has also been found that oximes of compound VII can be prepared by either electrochemical or catalytic reductive means. When employing catalytic reductive procedures, the preferred catalyst is the so-called "Lindlar catalyst". A typical Lindlar-type catalyst is lead poisoned palladium. The lead poisoned partially deactivates the palladium.

When carrying out electrochemical reductive procedures, an electrolysis cell with a mercury pool as the cathode and a Pt-anode is employed. A 0.5 molar lithium chloride solution in acetic acid serves as the electrolyte. Reduction of the nitro group to the oxime occurs at approximately 0.45 volts.

The cyano analogues, compounds of the formulae:

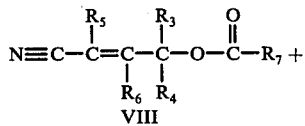

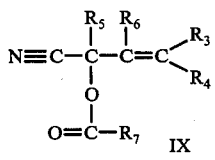

wherein $R_3$, $R_4$, $R_5$, $R_6$ and $R_7$ are as defined above, are generally prepared by reacting either of compounds II or III where $R_1 = R_2 = H$ with phosphorus trichloride in pyridine. Where the cyano derivative of the primary nitro esters is desired, i.e., compound VIII, either compound II or a crude mixture of compounds II and III may be employed as the starting material. It has been found that when the crude mixture is employed, the resultant product is substantially compound VIII. In order to obtain compound IX, it is therefore necessary to isolate compound III prior to the phosphorus trichloride treatment.

The reactions to form either of compounds VIII or IX are carried out employing pyridine as solvent and at a temperature ranging from about 20°-95° C., preferably 20°-25° C. and atmospheric pressure. Although pyridine is preferred, other nitrogenous bases may be employed. Other nitrogen bases that may be employed are quinoline, lutidine and picoline.

The transformation of nitro compounds, according to the foregoing procedure, has been found to be applicable in general to primary nitro compounds containing the —CH$_2$—NO$_2$ moiety. As an additional embodiment of this invention, compounds of the formula:

$$R_{10}—CH_2NO_2 \qquad X$$

wherein $R_{10}$ is a straight or branched chain alkyl group or alkylene group, cyclohexenyl or substituted cyclohexenyl, phenyl or substituted phenyl, may be transformed to compounds of the formula:

$$R_{10}—CN \qquad Xa$$

wherein $R_{10}$ is as defined above.

$R_{10}$ may typically have as substituents halogen, lower acyloxy, lower alkoxy, and lower alkoxycarbonyl. Compounds of formula Xa are prepared from compounds of formula X in accordance with the same conditions as the formation of compound VIII and compound II. The compounds of formula VIII are useful useful as polymer crosslinking or reactive dye agents.

A further embodiment of the instant invention is the preparation of γ-acetoxytiglic aldehyde, a compound of the formula:

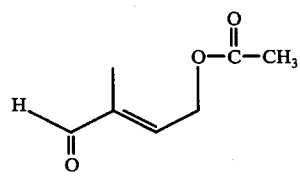

from compound II or a crude mixture of compounds II and III.

It should be noted at the outset that compound XI may be prepared from pure compound II or a crude mixture of compounds II and III. Compound XI cannot be prepared from pure compound III without first rearranging it to compound II. When preparing compound XI from a crude mixture of compounds II and III, the reaction conditions are such that III is initially rearranged to II. For best results, however, compound II should preferably be in the trans configuration.

In accordance with the instant invention, compound XI may be prepared according to either reductive or oxidative procedures.

One method of preparing compound XI is to treat compund II, or a crude mixture thereof with compound III, with from about 0.1 to 10 moles, preferably 2 to 10 moles, of a Group IV metal salt, preferably titanium trichloride, in the presence of pyridine. Temperature and pressure are not critical. The reaction is generally conducted at room temperature and atmospheric pressure. Compound XI is obtained in good yield and is substantially pure.

Compound XI may alternatively be prepared by treating compound II, or a crude mixture thereof with compound II, with metallic iron (group VIII-metal) or metallic zinc (group II-metal) in the presence of a lower alkyl mono-carboxylic acid, preferably acetic acid. The reaction may be conducted under reflux conditions resulting in a substantial yield of product. The product may be further purified according to conventional purification methods. It has been found that the oxime (compound VII) is an intermediate in the transformation of compound II to a compound XI in reductive processes.

Although organic solvents are generally employed, the preparation of compound XI can be effected in aqueous solvents under certain conditions. If the reaction is carried out under pH conditions of 2-4, treatment of compound II (or a crude mixture with III) with iron filings or zinc powder will produce compound VII and XI. If the pH range is not maintained, the starting material, compound II or the crude mixture with III, will be degraded. Any conventional acid that will maintain a pH range of 2-4 may be used, although mineral acids, especially HCl, are preferred. The resulting product may be purified according to conventional procedures.

The presence of base in the foregoing procedures, particularly pyridine and sodium bicarbonate have been found to enhance the rate of reduction of compound II (or a crude mixture thereof with compound III) to compound XI.

Compound XI may be prepared oxidatively by treating compound II (or a crude mixture thereof with compound III) with dipyridinium-chromiumtrioxide complex in the presence of an excess of pyridine. The reaction is generally carried out at room temperature and atmospheric pressure, although temperatures and pressure are not critical.

Compound XI may also be prepared by treating compound II (or a crude mixture thereof with compound III) with ozone (or an ozone-oxygen mixture of ratio of about 20:1) in the presence of from 0.1 to 1.1 moles of sodium bicarbonate. The presence of sodium bicarbonate in the reaction mixture has been found to enhance the oxidation of compound II (or a crude mixture thereof with compound III) to compound XI.

It has been found that under certain conditions of transforming compound II (or a crude mixture thereof with a compound III) to compound XI, there can be obtained a compound of the formula:

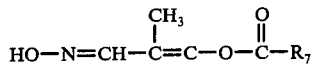

XII wherein $R_7$ is lower alkyl.

Compound XII may be obtained when compound II (or a crude mixture with compound III) is reduced catalytically with a Lindlar catalyst, electrolytically or when treated with metallic magnesium in the presence of a lower alkylmonocarboxylix acid, preferably acetic acid. When the reduction is carried out electrolytically, a bath comprising 0.5 molar LiCl in acetic acid is preferably employed. Other conventional electrolytic cells are usable. The electrodes generally employed are Hg-pool-cathode/Pt-anode; and the voltage is from about 0.35 to about 0.55, preferably 0.45 volts as measured against an Ag/AgCl reference electrode.

The above described procedures for the preparation of the nitro esters, derivatives thereof and γ-acetoxytiglic aldehyde may be carried out batchwise or continuously thus allowing for either small or large scale production.

The following non-limting examples illustrate the instant invention. All temperatures are in degrees Centigrade and the ether used is diethyl ether.

The following examples illustrate the nitroacyloxylation of isoprene.

EXAMPLE 1

To 2000 ml. (21.2 m) of acetic anhydride was added with stirring and cooling 270 g. (3 m) of 70% nitric acid. The rate of addition was adjusted so that the temperature was kept in the range of 15°–25°. On this scale the addition of nitric acid was completed in one hour. This mixture was stirred for an additional 1 to 2 hours at room temperature. 100 g. (1.47 m) of isoprene were added dropwise, with ice cooling. The clear yellow reaction mixture was stirred for an additional hour at room temperature and then poured into 4 liters of ice and water. The nitro compound, which separated as a yellow oil heavier than water, was separated; the water layer extracted with methylene chloride, all organic layers combined, washed with water and dried over magnesium sulfate. After distillation of the solvent and excess acetic anhydride in vacuum (max. distillation temperature 60° C.) a yellow oily residue of 207.9 g. was obtained.

The isomeric nitro compounds were separated by column chromatography.

The physical chemical constants for compound II are as follows:

$C_7H_{11}NO_4$: calculated: C 48.55, H 6.40, N 8.01. found: C 47.76, H 6.40, N 8.25.

The physical chemical constants for compound III are as follows:

$C_7H_{11}NO_4$: calculated: C 48.55, H 6.40, N 8.09. found: C 48.57, H 6.64, N 8.01.

EXAMPLE 2

A 5 l. 3-necked flask was charged with 3 l. (31.76 m) of acetic anhydride. Under stirring and ice cooling, 315 g. of 90% (4.5 m) nitric acid were added over a one hour period at a temperature not exceeding 30° C. After additional 2 hours, stirring at room temperature, 150 g. (2.2 m) of isoprene were added dropwise, under cooling at ca. 20° over a 1 hour period. The reaction was worked up in the same manner as described in example 1. 326 g. of crude nitro compounds were obtained. A vapor phase chromatogram revealed the ratio of II to III to be ca. 7:3.

EXAMPLE 3

Following the procedure of Example 2, 500 cc (5.3 m) of acetic anhydride was reacted first with 100 g. of 90% nitric acid (1.4 m) followed by 68 g. (1 m) of isoprene. Work up as in Example 2 yielded the crude nitro compounds in the isomer ratio of ca. 7:3.

EXAMPLE 4

Following the procedure of Example 2, 500 cc (5.3 m) of acetic anhydride were reacted with 68 g. (0.96 m) of 90% nitric acid followed by 68 g. (1 m) of isoprene. Work up as in Example 2 yielded a reaction mixture with an isomer ratio of ca. 7:3.

EXAMPLE 5

To 500 ml. (5.3 m) of acetic anhydride were added, over one hour, under stirring and cooling, 100 g. (1.4 m) of 90% nitric acid at 18°–25°. After an additional hour, 68 g. (1 m) of isoprene were added dropwise with stirring at 18°–25°. The mixture was stirred for 1 hour at room temperature before it was poured onto 1.5 l. of ice. It was extracted in the cold with methylene chloride, washed with ice water and dried over $MgSO_4$. The solvent was removed on the rotary evaporator at max 40° C. To the residue was added 54.3 g. of water and the mixture stirred at room temperature for 48 hours. A sample of this mixture, after dilution with water, extraction with $CH_2Cl_2$ and cold (and rapid) bicarbonate wash showed a ratio of isomers of 7:3 for II and III respectively.

EXAMPLE 6

Following the procedure of Example 1, with the exception that after the addition of isoprene, the reaction mixture was stirred overnight at room temperature before work up. The isomer ratio of II:III was ca. 7:3 as determined by vapor phase chromatography.

The following examples illustrate the nitroacyloxylation of conjugated dienes other than isoprene.

EXAMPLE 7

To 166 ml. of acetic anhydride was added 90% nitric acid (27.7 g.) under cooling at 25° C. over a 45 minute period. After an additional 5 minutes of stirring 20 g. of 1,3-hexadiene was added dropwise at 25° C. over 1 hour. Ice cooling was employed as required. The reaction was completed by stirring the mixture for an additional hour, followed by quenching in ice and water. Extraction with methylenechloride, washing with water, drying of the organic layers over anhydrous sodium sulfate and evaporation of the solvent and excess acetic anhydride resulted in 47.0 g. of a crude reaction product. Column chromatography and careful bulb to bulb distillation (oven 120° C., 0.5 mmHg) yielded actic acid (1-nitro-2-hexen-4-yl)ester.

EXAMPLE 8

To acetic anhydride (142 ml.) was added dropwise 90% $HNO_3$ (23.6 g.) at 25° C. (ice-cooling) over 40 minutes. To this mixture was dropped 20 g. of 2,4-dimethyl-1,3-pentadiene over a 1 hour period at 25° C. (ice bath cooling required). Work up as described in Example 7 yielded 40.4 g. of the crude acetic acid(2,4-dimethyl-5-nitro-pent-3-en-2-yl)ester. Purification was achieved by column chromatography.

EXAMPLE 9

To 1350 ml. of acetic anhydride was added dropwise under stirring and cooling 115 g. of 90% nitric acid. Over the next two hour period 50 g. of 1,3-butadiene was bubbled into the reaction mixture at 22°–25° C. After stirring an additional 30 minutes the reaction was quenched with ice and worked up in Example 7. A crude product (110 g.) containing a mixture of acetic acid(4-nitro-but-1-en-3-yl)ester and acetic(4-nitro-but-2-en-1-yl)ester was obtained.

EXAMPLE 10

To 166 ml. of acetic anhydride were dropped 27.7 g. 20% nitric acid at 25° C. under ice cooling over a 45 minute period. This was followed by the hour long addition of 19.5 g. of 1,3-cyclo hexadiene at 25° C. (ice cooling from time to time). After an additional hour stirring the reaction was poured onto ice and worked up as above. Purification over silicagel yielded acetic acid (4-nitro-cyclohex-2-en-1-yl)ester as a cis/trans mixture.

EXAMPLE 11

To acetic anhydride (166 ml.) was dropped 90% nitric acid (27.7 g.) at 25° C. over a 1 hour period (ice cooling is required). This is followed by the dropwise addition of 2,5-dimethyl-2,4-hexadiene over 1 hour at 25° C. After an additional hour stirring at this temperature the reaction mixture was quenched on ice and worked up according to the procedure of Example 7. A crude product weighing 51.3 g. was obtained.

Purification via column chromatography yielded acetic acid(2,5-dimethyl-5-nitro-hex-3-en-2-yl)ester as a yellow oil.

EXAMPLE 12

Acetic anhydride, 1000 ml. (10.58 m.) was stirred and under cooling 135 g. (1.5 m.) of 70% nitric acid was added at such a rate that the temperature did not exceed 25° C. After one hour, with additional stirring, 50 g. (0.74 m.) of isoprene were added at a temperature from 15°–22° C. over a period of approximately 30 minutes. After work up, the crude nitroacetates were added to a solution of 150 g. of concentrated sulfuric acid in 1 l. of methanol. After standing overnight at room temperature, the mixture was poured onto 2 liters of water, NaCl was added to saturation and the products were extracted with methylene chloride. Purification and separation of the two nitro alcohols was achieved by column chromatography using silica gel as adsorbent and benzene/ethylacetate as eluting solvents. The physical chemical properties were in accord with the depicted structures IV and V.

EXAMPLE 13

The following example illustrates the antibacterial activity of compounds II–V. The compounds were tested against the following organisms (in vitro), *Escherichia coli, Staphylococcus aureus, Pseudomonas aeruginosa* and *Proteus vulgaris,* according to the following procedure:

Compounds are prepared as a 6% solution in a suitable solvent such as water, ethanol or dimethylformamide. The 6% stock solution is then 5-fold serially diluted in test tubes to give the desired concentrations when mixed with agar and poured into sterile Petri dishes. Tryptone glucose extract agar is used as a medium for the bacterial testing. The plates are spot inoculated with a 24-hour nutrient broth culture of the bacteria to be tested and incubated at 37° C. for 48 hours. The plates are then examined visually for bacteria growth. The results, expressed in minimum inhibitory concentration in micrograms/ml (MCG/Ml) are tabulated in Tables I–IV.

Table I

| ORGANISM | Compound II MCG/ml |
|---|---|
| E-COLI | 15.4 |
| STAPH-AU | 76.8 |
| PS-AERUG | 76.8 |
| P-VULGAR | 15.4 |

Table II

| ORGANISM | Compound III MCG/ml |
|---|---|
| E-COLI | 76.8 |
| STAPH-AU | 76.8 |
| PS-AERUG | 76.8 |
| P-VULGAR | 15.4 |

Table III

| ORGANISM | Compound IV MCG/ml |
|---|---|
| E-COLI | 76.8 |
| STAPH-AU | 76.8 |
| PS-AERUG | 84.0 |
| P-VULGAR | 76.8 |

Table IV

| ORGANISM | Compound V MCG/ml |
|---|---|
| E-COLI | 76.8 |
| STAPH-AU | 76.8 |
| PS-AERUG | 76.8 |
| P-VULGAR | 76.8 |

EXAMPLE 14

The following example illustrates the antifugal activity of Compounds II-V. The compounds were tested against the following organisms (in vitro), *Aspergillus niger, Pencillium piscarium, Aspergillus oryzae* and *Aureobasidium pullulans,* according to the following procedure:

Compounds are prepared as a 6% solution in a suitable solvent such as water, ethanol, or dimethylformamide. The 6% stock solution is then 5-fold serially diluted in test tubes to give the desired concentrations when mixed with agar and poured into sterile Petri dishes. Mildew glucose agar is used as a nutrient medium for the fungal testing. The plates are spot inoculated with spore suspensions of the fungi. The plates are then incubated at 28° C. for 7 days. The plates are examined visually for growth. The results are tabulated in Tables V-VIII.

Table V

| ORGANISM | Compound II MCG/ml |
|---|---|
| A-NIGER | 0.12 |
| PEN-PISC | 0.03 |
| ASP-ORYZ | 0.03 |
| A-PULL | 0.03 |

Table VI

| ORGANISM | Compound III MCG/ml |
|---|---|
| A-NIGER | 0.02 |
| PEN-PISC | 0.03 |
| ASP-ORYZ | 0.03 |
| A-PULL | 0.03 |

Table VII

| ORGANISM | Compound IV MCG/ml |
|---|---|
| A-NIGER | 0.61 |
| PEN-PISC | 0.12 |
| ASP-ORYZ | 0.12 |
| A-PULL | 1.2 |

Table VIII

| ORGANISM | Compound V MCG/ml |
|---|---|
| A-NIGER | 3.1 |
| PEN-PISC | 3.1 |
| ASP-ORYZ | 3.1 |
| A-PULL | 3.1 |

The following examples illustrate the preparation of nitrile compounds from primary nitro compounds.

EXAMPLE 15

To 1-Nitrododecane (2.013 g.), dissolved in 20 ml. of pyridine was added 0.81 cc of phosphorous trichloride. The mixture was stirred overnight at 95°, quenched on ice, acidified with 6N HCl and the product extracted with ether. After Kugelrohrdistillation (oven temperature 140°, 1 mmHg), 1.245 g. (73%) of dodecanoic acid nitrile as a colorless liquid was obtained.

EXAMPLE 16

(p-Methoxyphenyl)-nitromethane (1.013 g.) in 10 cc of pyridine was reacted with 0.5 cc of $PCl_3$ in an ice bath. The temperature rose at 60°. This temperature was maintained for one hour under magnetic stirring. Work up followed by sublimation (oven temperature 130°, 1 mmHg) yielded 0.565 g. (77%) of crystalline p-methoxybenzonitrile, m.p. 53.5°–56°. Crystallization from hexane increased the melting point to 57.5°–59°.

EXAMPLE 17

Phenylnitromethane (2.0 g.) in 20 cc of pyridine was reacted under ice cooling with 1.27 cc of $PCl_3$. The internal temperature rose at 60°. Stirring was continued at 60° for 10 minutes before the reaction was quenched with ice. Work up followed by distillation (kugelrohr, oven at 120°, 1 mmHg vacuum) yielded 0.927 g. (62%) of colorless benzonitrile.

EXAMPLE 18

(1-Acetoxycyclohexyl)-nitromethane (0.857 g.), dissolved in 9 cc of pyridine was reacted with 0.4 cc of phosphoroustrichloride for 6 hours at 60°. Work up as described for Example 17 followed by kugelrohr distillation at oven temperature of 110° and 0.1 mmHg yielded 0.405 g. of cyclohexane cyanohydrin acetate.

EXAMPLE 19

To 1-acetoxy-4-nitro-but-2-ene (4 g.) in 40 cc of methylenechloride and 40 cc of pyridine was added under ice cooling 4.4 cc of $PCl_3$. The reaction was worked up after 1 hour stirring at room temperature. The crude product was purified by distillation and column chromatography. γ-Acetoxycrotononitrile was obtained as a colorless liquid.

EXAMPLE 20

11.4 g. of crude 1-nitro-2-acetoxy-hex-5-ene was dissolved in 100 ml. of pyridine and reacted with 10 cc of $PCl_3$ (ice bath cooling is required during the dropwise addition of $PCl_3$) at room temperature overnight. Work up followed by chromatography and high vacuum distillation yielded 3.2 g. of 5-acetoxy-5-cyano-pent-1-ene of approximately 70% v.p.c. purity. An analytically pure sample was obtained via thick layer chromatography.

EXAMPLE 21

To 3-chloronitropropane (2.015 g.) in 20 cc of pyridine was added 1.5 ml. of phosphorous trichloride. The mixture was stirred at room temperature for 1 day. Work up as described in Example 17 followed by kugelrohr distillation (oven temperature 60°–80°/15 mm) yielded 0.613 g. (42%) of β-chloropropionitrile as a colorless liquid.

EXAMPLE 22

4-Nitrobutyric acid methylester (1.999 g.) was dissolved in 20 ml. of pyridine and reacted with 1.2 ml. of phosphorous trichloride at room temperature over a weekend. An additional 0.4 ml. of $PCl_3$ was added and the reaction was heated for 5 hours at 50° C. Work up as in Example 17 followed by kugelrohr distillation yielded 0.661 g. (43%) of β-cyano-methylpropionate.

EXAMPLE 23

Heptanoic acid(6-acetoxy-7-nitro)methyl ester (4.0 g.) was dissolved in 20 ml. of methylene chloride and 1.4 g. of PCl₃ was added at 20°–25°. At the same temperature 20 ml. of pyridine was added (external cooling is required) and the reaction was stirred overnight at room temperature. Work up as described in Example 17 yielded a crude residue of 2.6 g. Kugelrohr distillation afforded 1.8 g. of colorless aldehydecyanohydrin acetate.

EXAMPLE 24

To 1.0 g. of 1-nitro-2-acetoxy-2-phenyl-ethane in 10 ml. of pyridine was added 0.5 ml. of PCl₃. After stirring at room temperature overnight, the reaction was worked up in the standard manner. There was obtained 0.619 g. of benzaldehyde cyanohydrin acetate.

EXAMPLE 25

(Cyclohex-1-en)-1-nitromethane (0.64 g.) in 6 ml. of pyridine was reacted with 0.4 ml. of PCl₃. After 1 day stirring at room temperature and standard work up there was obtained 0.210 g. of 1-cyano-cyclohex-1-ene.

EXAMPLE 26

The following example illustrates the preparation of acetic acid (3-methyl-4-amino-2-buten-1yl) ester.

To 500 mg. (0.003 m) of acetic acid (3-methyl-4-nitro-2-buten-1-yl) ester was added 10 ml. of ethanol and 1 g. (0.015 m) of zinc powder followed by addition of 5 ml. (0.225 m) of concentrated HCl under magnetic stirring via a pipette. The reaction mixture which heated up rapidly was quenched in ice and ammonia after approximately 2 minutes stirring. The reaction mixture was subsequently extracted with ether and the solvent removed in vacuo. A yellow oil resulted which was purified via distillation at b.p. 64°/0.1 mmHg. Analytical purification was achieved via silica gel chromatography using ethylacetate as eluting solvent.

EXAMPLE 27

This example illustrates the preparation of oxime derivatives of acetic acid (3-methyl-4-nitro-2-buten-1-yl)ester.

A mixture of 1040 mg. (0.006 m) of acetic acid (3-methyl-4-nitro-2-buten-1-yl)ester. 10 cc of 96% (0.21 m) acetic acid and 672 mg. (0.012 m) iron shavings was heated at 80° for 5 hours and allowed to stand overnight at room temperature. The mixture was then filtered and the excess acetic acid evaporated under vacuum at max. 50° C. The residue was then worked up by adding ice and water, neutralized with sodium bicarbonate and extracted with ether. After evaporating the organic solvent, the oxime was isolated via thick layer chromatography. Slightly off white crystals (m.p. 58°–63°) were obtained. The nmr spectrum of this material showed trace impurities to be present. The major absorption bands, however, were superimposable with the spectrum obtained from a pure sample prepared from γ-acetoxytiglic aldehyde and hydroxylamine. This preparation is illustrated hereinafter.

EXAMPLE 28

This example illustrates the preparation of acetic acid (3-methyl-3-cyano-2-propen-1-yl)ester.

To 500 mg. (0.003 m) of acetic acid(3-methyl-4-nitro-2-buten-1-yl)ester in 10 ml. of pyridine was added, under an atmosphere of nitrogen, 8 ml. of a 10% solution of phosphorous trichloride (0.008 m) in methylene chloride. After standing for 1 hour at room temperature the reaction mixture was poured, under cooling, into 3N HCl. The reaction mixture was then extracted with ether, washed with saturated sodium chloride solution and dried over magnesium sulfate. The solvent was then evaporated after filtration of the drying agent. The acetic acid (3-methyl-3-cyano-2-propen-1-yl)-ester obtained as a yellow oily residue was purified via vacuum distillation, b.p. 63°/0.05 mmHg.

EXAMPLE 29

The following example illustrates the obtention of the cyano derivative of Example 2 when a crude mixture of acetic acid (3-methyl-4-nitro-2-buten-1-yl)ester and acetic acid (3-methyl-4-nitro-1-buten-3-yl) ester are treated in general accordance with the procedure of Example 28.

A crude mixture of acetic acid (3-methyl-4-nitro-2-buten-1-yl)ester and acetic acid (3-methyl-4-nitro-1-buten-3-yl)ester (ratio of ca. 7:3) (20 g.) was diluted with 400 ml. of pyridine. To this mixture was added dropwise, over a five minute period, 32 g. of PCl₃. The temperature rose to 95°. Stirring was continued over a period of 1 hour and the temperature allowed to drop to 20°. Under cooling, the mixture was diluted with 500 ml. of ice water and 500 cc of concentrated HCl added. The product was isolated via ether extraction, distillation and purification via chromatography over silica gel.

EXAMPLE 30

This example illustrates the preparation of acetic acid (3-methyl-3-cyano-1-propen-3-yl)ester from acetic acid (3-methyl-4-nitro-1-buten-3-yl)ester.

30 g. (0.17 m) of acetic acid (3-methyl-4-nitro-1-buten-3-yl)ester was diluted with 600 cc of pyridine. To this was added dropwise a solution of 50 g. (0.32 m) PCl₃ in 50 cc of CH₂Cl₂ over a ½ hour period. The mixture was stirred overnight at room temperature. Ice, followed by 600 ml. concentrated HCl, was subsequently added to the reaction mixture. Extraction with ether and chromatographic separation of the crude product yielded acetic acid (3-methyl-3-cyano-1-propen-3-yl)ester as a colorless oil.

The following examples illustrate the preparation of γ-acetoxytiglic aldehyde in accordance with the instant invention.

EXAMPLE 31

To a solution of 2 g. (0.12 m) of acetic acid (3-methyl-4-nitro-2-buten-1-yl)ester, 80 ml. of tetrahydrofuran were added 11.96 g. (0.015 m) of pyridine in 80 ml. of water. The mixture was stirred in 500 ml. 3-necked flask fitted with an argon bubbler and a dropping funnel. Over a 4 hour period 33.52 ml. of a 20% titaniumtrichloride solution (equivalent to 0.34 m) diluted to 80 ml. with water was added dropwise. A precipitate formed and the entire mixture was stirred overnight at room temperature under an argon atmosphere. The reaction was then worked up by saturating with NaCl and then followed by repeated extractions with ether. After drying the organic layers over anhydrous magnesium sulphate and evaporation of the solvent an oily brown residue was obtained. Purification was achieved by distillation. γ-Acetoxytiglic aldehyde was obtained in an analytically pure form after crystallization from ether at −70° C.

EXAMPLE 32

Dipydridinium-chromiumtrixodie complex 258 mg. (0.0008 m) in 5 ml. of pyridine was added to 346 mg. (0.002 m) of acetic acid (3-methyl-4-nitro-2-buten-1yl)ester and stirred overnight. Aqueous work up provided crude γ-acetoxytiglic aldehyde as determined by vapor phase chromatographic analysis.

EXAMPLE 33

To 500 mg. (0.003 m) of iron filings in 4 ml. of acetic acid was added 173 mg. (0.001 m) of acetic acid (3-methyl-4-nitro-2-buten-1yl) ester in 1 ml. of acetic acid. After 30 minutes reflux, the mixture was quenched in ice and the product isolated via extraction with $CH_2Cl_2$. A crude residue of 93 mg. of γ-acetoxytiglic aldehyde was obtained, 71.5% yield.

EXAMPLE 34

34.6 g. of a crude mixture of nitroacetates in 60 g. of acetic acid was added to 50 g. of iron filings in 300 ml. of 98% acetic acid at ca. 100°–120° (oil bath set at 120° ) over a 2-3 min. period. The mixture turned dark in color, some brown nitric fumes developed at the beginning and a temperature rise to reflux was observed. After 15 minutes stirring at this temperature, the mixture was cooled, filtered and the excess acetic acid removed under vacuum. Pure γ-acetoxytiglic aldehyde was isolated via steam distillation of the resulting residue, extraction from the water distillate with methylene chloride, distillation and low temperature (−70° ) crystallization from ether.

EXAMPLE 35

This example illustrates the preparation of γ-acetoxytiglic aldehyde from a crude mixture of acetic acid (3-methyl-4-nitro-2-buten-1-yl)ester and acetic acid (3-methyl-4-nitro-1-buten-3-yl)ester utilizing water as a solvent.

To a mixture of 10 g. of iron filings (40 mesh) and 50 cc of water was added 10 g. of a mixture of crude nitroacetates. Under stirring and cooling in a water bath, a total of 35 ml. of 4n HCl was added dropwise at a pH of between 2 to 4. The color of the reaction mixture turned brown. After removing excess iron, by filtration, the reaction was worked up via ether extraction yielding γ-acetoxytiglic aldehyde.

EXAMPLE 36

11 g. of acetic acid(3-methyl-4-nitro-2-buten-1-yl)ester was dissolved in 50 cc of acetic acid and 5 g. Zn powder added. The reaction mixture was stirred for 2 hours at room temperature followed by steam distillation. A crude $C_5$-aldehyde showing the same retention time on v.p.c. as authentic γ-acetoxytiglic aldehyde was extracted.

EXAMPLE 37

This examples illustrates the preparation of γ-acetoxytiglic aldehyde by ozonolysis.

A slow stream of an ozone-oxygen mixture was passed through a solution of acetic acid( 3-methyl-4-nitro-2-butenyl-1-yl)ester (173 mg.) in 20 ml. of ethanol containing 100 mg. of sodium bicarbonate. Quenching with a small amount of sodium-hydrogensulfite followed by v.p.c. analysis revealed the presence of γ-acetoxytiglic aldehyde.

EXAMPLE 38

The following examples illustrates the preparation of trans γ-acetoxytiglic aldehyde from the oxime analogue of the primary nitroacetate. 314 mg. of acetic acid (3-methyl-4-oxime-2-buten-1-yl)ester was stirred at 115° C. in a mixture of 10 ml. 96acetic acid and 1 g. of iron filings. After 30 minutes, the reaction was cooled to room temperature, filtered and the solids washed with acetic acid followed by ether. Excess solvents were evaporated under vacuum at 40° bath temperature, then was dissolved in ether and washed with saturated sodium-bicarbonate solution. The organic layer was dried and a residue of 253 mg. of trans γ-acetoxytiglic aldehyde was obtained.

EXAMPLE 39

Acetic acid(3-methyl-4-nitro-2-buten-1yl)ester (1.73 g.) in 20 m. of acetic acid was stirred for one hour in an ice bath in the presence of 0.24 g. of magnesium turnings. TLC after 1 hour revealed the presence of γ-acetoxytiglic aldehyde oxime.

EXAMPLE 40

Acetic acid(3-methyl-4-nitro-2-butenyl)ester was electrolyzed in 0.5 molar LiCl in acetic acid at 0.45 volt (Electrodes Hg-pool; Pt; Agcl). γ-Acetoxytiglic aldehyde oxime was detected via thin layer chromatography, using silicagel plates and the system benzene/ethylacetate 4:1. Short UV light served as viewing method.

EXAMPLE 41

3.46 g. of acetic acid(3-methyl-4-nitro-2-butenyl)ester in 50 ml. of tetrahydrofuran and 5 cc of acetic acid was hydrogenated at 50 psi in the presence of lead poisoned palladium catalyst. γ-acetoxytiglic aldehyde oxime identified via thin layer chromatography and n.m.r. spectroscopy.

EXAMPLE 42

This example illustrates the rearrangement of the tertiary nitroacetate to the primary nitroacetate. 100 mg. of pure acetic acid (3-methyl-4-nitro-1-buten-3-yl)ester was heated for approximately 16 hours at 75° in 1 ml. of 0.63% $H_2SO_4$ in acetic acid. VPC analysis showed all of the tertiary acetate to have rearranged to the (3-methyl-4-nitro-2-buten-1-yl)ester being formed. Evidence of VPC and nmr data would indicate that approximately one-third of the product is in the cis configuration.

EXAMPLE 43

200 mg. of a crude 7:3 mixture of the primary and tertiary nitroacetates were heated at 70° to 75° in a mixture of 2 cc of 0.63% $H_2SO_4$ in acetic acid in the presence of 2 crystals of copper sulfate. Vpc-samples, worked up via neutralization with sodium bicarbonate and ether extraction, showed the ratio of the primary acetate to the tertiary acetate to have changed to 90:10 after 3 hours and 95:5 after 6 hours.

EXAMPLE 44

200 mg. of crude 7:3 mixture of the primary and tertiary nitroacetates (compounds II and III) were heated for 6 hours at 75° in 2 ml. of 0.63% $H_2SO_4$ in acetic acid. Work up of a small portion of the resulting product as in Example 43, showed ca. 5% of unchanged tertiary nitroacetate left in the reaction mixture was determined by vapor phase chromatography.

EXAMPLE 45

This example illustrates that the γ-acetoxytiglic aldehyde can be readily transformed to the acetic acid (3-methyl-4-oxime-2-buten-1-yl)ester.

Hydroxylamine hydrochloride (100 g.), pyridine (500 ml.) and 100 g. γ-acetoxytiglic aldehyde were refluxed for 2 hours in 500 ml. of ethanol. After cooling to room temperature, the reaction mixture was evaporated at 50° water bath in the high vacuum. To the residue was added 500 ml. water and the product was extracted with ether. The combined organic phases were evaporated to an oily residue to which was added 50 cc alcohol followed by 200 cc of water. The oxime crystallized by chilling in an ice bath. The crude product was recrystallized from ether. A first crop of 37 g., m.p. 67°–68°, of pure oxime of acetic acid (3-methyl-4-nitro-2-buten-1-yl)ester was obtained.

$C_7H_{11}NO_3$: calcd: C 53.49, H 7.06, N 8.91. Found: C 53.68, H 7.31, N 8.91.

The following examples illustrate the preparation of 2-acetoxytiglic aldehyde from isoprene.

EXAMPLE 46

To 90 ml. of acetic anhydride was added dropwise under stirring and cooling at 23°–25° 15 g. of 90% nitric acid over a period of 40 minutes. After an additional 5 minutes of stirring the dropwise addition of 8.98 g. of isoprene was started. There is a considerable exotherm and the temperature during the 1 hour addition is controlled at 25° +3° with the aid of an adjustable ice bath. The stirring is extended in additional hour at 25° after completion of the addition of isoprene. The reaction is then quenched in ice and water, and extracted with methylenechloride. The extracts are washed with ice water combined and dried over magnesium sulfate. Evaporation at 50° on a rotary evaporator, first with water pump vacuum (solvent) followed by high vacuum (excess acetic anhydride), yielded an orange oily residue of 23.1 g. (crude nitroacetylation products). The above residue was dissolved in 71.5 ml. acetic acid and 0.97 g. of concentrated sulfuric acid was added. The mixture was kept at 75° in an oil bath overnight. To this rearranged reaction mixture was added 78.5 ml. of acetic acid, 1.03 g. of sodium carbonate (anhydrous), 9.2 g. of pyridine followed by 22 g. of iron filings mesh 40. Under good stirring the reaction temperature is maintained between 85°–88° which required alternate heating and cooling periods. After a total reaction time of 1 hour, the dark brown mixture is cooled to room temperature in an ice bath, filtered over a pad of celite and washed with methylene chloride. After evaporation of solvent and excess acetic acid on a rotary evaporator (50°, water aspirator) a black residue of 115 g. is obtained. This is dissolved in 150 ml. of water, followed by the addition of 20 ml. of 37% formaldehyde solution and 150 ml. of 1 m $H_2SO_4$ to adjust the pH to 2.5. Rapid steam distillation for 1 hour yielded close to 2 liters of slightly yellow condensate. Extraction with methylene chloride, drying over $MgSO_4$ and evaporation yielded a crude, light yellow residual oil of 9.97 g. Kugelrohr distillation (oven at 145°; water pump vacuum) gave a faintly yellow colored distillate of 9.156 with v.p.c. purity of 93.6%. The overall chemical yield, based on, isoprene is calculated at 45.7% γ-acetoxytiglic aldehyde.

EXAMPLE 47

Into a 2 l three-necked flask, equipped with a mechanical stirrer, thermometer and 125 ml. size dropping funnel was placed 680 ml. of acetic anhydride. Over a 45 minute interval 113 g. of 90% $HNO_3$ was added under cooling at 23°–25° (ice bath). After 5 minutes additional stirring 68 g. of isoprene were added dropwise over a 1 hour period. The temperature was controlled with an ice bath and kept between 23°–25° at all times. After 2 hours additional stirring at 25°, the reaction was quenched in ice and water, and extracted with methylene chloride. The combined organic phases were dried over anhydrous sodium sulfate and evaporated first at 40° and water aspirator and later at 40°–48° under high vacuum to remove excess of acetic anhydride. The residue, 182.3 g. of yellow oil, was dissolved in 540 ml. of acetic acid and 7.3 g. of concentrated sulfuric acid was added. The homogeneous mixture was kept overnight at 75° oil bath temperature with slow stirring. Next morning was added 7.8 g. of anhydrous sodium carbonate, 540 ml. of toluene and 160 g. of iron filings 40 mesh. The oil bath temperature was raised to 98° and when the internal temperature reached 83°, 20 g. of anhydrous sodium carbonate was added. After 80 minutes at 86°–89° (ice-cooling is necessary at intervals) and vigorous stirring the reduction was complete as judged by vpc. The dark reaction mixture was cooled to 20°, filtered over a pad of celite and the inorganic washed with methylene chloride. The solvents, including excess of acetic acid were evaporated on a rotary evaporator at 45° bath temperature. To the black residue, 397 g., were added 500 ml. of water, 100 ml. of 37% formaldehyde solution and 215 ml. of sulfuric acid solution made up from 600 ml. of water and 125 g. of concentrated sulfuric acid. This brought the pH of the reaction to 2.5. Steam distillation after one hour yielded approximately 3 liters of distillate. The distillation was continued for another two hours and a 3 liter and a 2 liter fraction of condensates were collected. Each of the condensates were extracted with methylene chloride. The first condensate (3 l) yielded 47.6 g., the second (3 l) 12.0 g. and the third (2 l) 1.8 g. of crude aldehyde. The total crude of 61.4 g. was distilled over a Vigreux column, b.p. 75°–80°, 0.5–1 mmHg (oil bath at 105°–120° C.). There was obtained 56.5 g. (40%) of γ-acetoxytiglic aldehyde with vpc purity of 97%.

I claim:

1. A process for the preparation of a compound having the formula

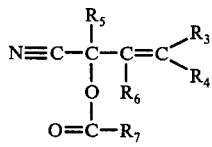

IX wherein $R_3$, $R_4$, $R_5$ and $R_6$ are hydrogen or lower alkyl and $R_7$ is lower alkyl
which comprises treating a compound having the formula

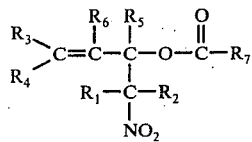 III wherein $R_1$ and $R_2$ are hydrogen; $R_3$, $R_4$, $R_5$ and $R_6$ are hydrogen or lower alkyl; and $R_7$ is lower alkyl with $PCl_3$ in the presence of pyridine, said treatment being conducted at a temperature ranging from 20°–95° C.

2. A process according to claim 1 wherein $R_3$, $R_4$ and $R_6$ are hydrogen and $R_5$ and $R_7$ are methyl.

3. A process for the preparation of a compound selected from the group consisting of those having the formula

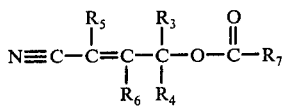 VIII or

 Xa wherein $R_3$, $R_4$, $R_5$ and $R_6$ are hydrogen or lower alkyl; and $R_7$ is lower alkyl; $R_{10}$ is a straight or branched chain alkyl group or alkylene group, cyclohexenyl or substituted cyclohexenyl, phenyl or substituted phenyl wherein said substitutents are selected from the group consisting of halogen, acyloxy groups having from 1–6 carbon atoms, lower alkoxy and lower alkoxycarbonyl which comprises treating a compound of the formula

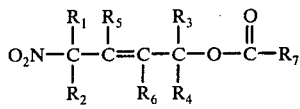 II or

 X wherein $R_1$ and $R_2$ are hydrogen; and $R_3$, $R_4$, $R_5$, $R_6$, $R_7$ and $R_{10}$ are as defined above with $PCl_3$ in the presence of pyridine, said treatment being conducted at a temperature ranging from 20°–95° C.

4. The process of claim 3 wherein $R_3$, $R_4$ and $R_6$ are hydrogen and $R_5$ and $R_7$ are methyl.

5. A process for the preparation of a compound having the formula

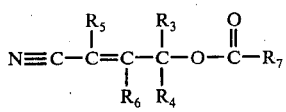 VIII wherein $R_3$, $R_4$, $R_5$ and $R_6$ are hydrogen or lower alkyl which comprises treating a mixture of compounds having the formula

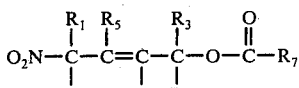 II

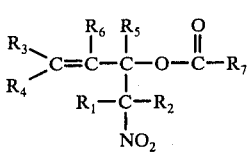 III wherein $R_1$ and $R_2$ are hydrogen, $R_3$, $R_4$ and $R_5$ are hydrogen or lower alkyl and $R_6$ is lower alkyl with $PCl_3$ in pyridine, said treatment being conducted at a temperature ranging from 20° to 95° C.

6. A process for the preparation of a compound having the formula:

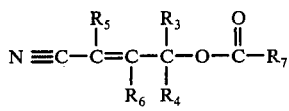 VIII wherein $R_3$, $R_4$, $R_5$ and $R_6$ are hydrogen or lower alkyl and $R_7$ is lower alkyl; which comprises treating a mixture of compounds having the formula:

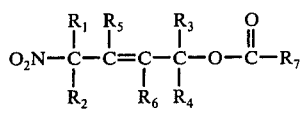 II

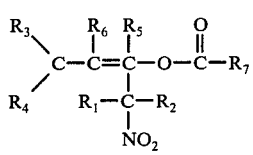 III wherein $R_1$ and $R_2$ are hydrogen and $R_3$, $R_4$, $R_5$, $R_6$ and $R_7$ are as defined above; with $PCl_3$ in pyridine, said treatment being conducted at a temperature ranging from 20° to 95° C.

7. A process according to claim 6 wherein $R_3$, $R_4$ and $R_6$ are hydrogen and $R_5$ and $R_7$ are methyl.

* * * * *